(12) United States Patent
Kitsugi et al.

(10) Patent No.: US 9,063,144 B2
(45) Date of Patent: Jun. 23, 2015

(54) DETECTION METHOD AND QUANTIFICATION METHOD FOR TARGET SUBSTANCE

(75) Inventors: Katsuhiko Kitsugi, Chiba (JP); Satoru Sugita, Chiba (JP); Noriyuki Ohnishi, Chiba (JP)

(73) Assignees: JNC Corporation, Tokyo (JP); Ortho-Clinical Diagnostics Kabushiki Kaisha, Tokyo (JP)

( * ) Notice: Subject to any disclaimer, the term of this patent is extended or adjusted under 35 U.S.C. 154(b) by 725 days.

(21) Appl. No.: 13/322,809

(22) PCT Filed: May 21, 2010

(86) PCT No.: PCT/JP2010/058651
§ 371 (c)(1),
(2), (4) Date: Nov. 28, 2011

(87) PCT Pub. No.: WO2010/137532
PCT Pub. Date: Dec. 2, 2010

(65) Prior Publication Data
US 2012/0070912 A1     Mar. 22, 2012

(30) Foreign Application Priority Data

May 29, 2009   (JP) ................................ 2009-130958

(51) Int. Cl.
| | | |
|---|---|---|
| *G01N 33/543* | (2006.01) | |
| *G01N 33/58* | (2006.01) | |
| *G01N 21/78* | (2006.01) | |
| *G01N 33/542* | (2006.01) | |

(52) U.S. Cl.
CPC .............. *G01N 33/583* (2013.01); *G01N 21/78* (2013.01); *G01N 33/542* (2013.01); *G01N 33/582* (2013.01)

(58) Field of Classification Search
None
See application file for complete search history.

(56) References Cited

U.S. PATENT DOCUMENTS 5,283,079 A * 2/1994 Wang et al. .................. 427/2.13
5,420,016 A * 5/1995 Boguslaski et al. ............ 435/12
5,998,588 A  12/1999 Hoffman et al.
2008/0220531 A1  9/2008 Stayton et al.
2010/0062433 A1 * 3/2010 Nagaoka et al. .................. 435/6

FOREIGN PATENT DOCUMENTS

| JP | 58-11575 B2 | 3/1983 |
| JP | 2006-145256 A | 8/2006 |
| WO | 2008/001868 A1 | 1/2008 |

OTHER PUBLICATIONS

Notice of Reasons for Rejection issued to CN Application No. 201080023788.8, mailed 22, 2014 along with (English translation), May 22, 2014.
Notice of Reasons for Rejection issued to CN Application No. 201080023788.8, mailed May 22, 2014 along with English translation, May 22, 2014.
Yi Lu, et al., Nanoparticles/Dip Stick, Methods Mol Biol, 2009, 535:223-239.
Office Action issued to CN Application No. 201080023788.8, mailed Nov. 13, 2013.
International Search report for PCT/JP2010/058651, mailed Jun. 15, 2010.

* cited by examiner

*Primary Examiner* — Gary W Counts
(74) *Attorney, Agent, or Firm* — Hoffmann & Baron, LLP

(57) ABSTRACT

Provided are a detection method and a quantification method for a detection target, which can detect and quantify the detection target rapidly, inexpensively, simply, and with high accuracy in a variety of environments. A method for detecting the detection target in a specimen includes processes in which there are mixed a first binding substance which binds a first material containing a stimuli-responsive polymer and a first affinity substance which has affinity for the detection target, a second binding substance which binds a hydrophilic second material and a second affinity substance which has affinity for the detection target, and a specimen; the resulting mixture is placed under conditions where the stimuli-responsive polymer agglutinates and the mixture is developed into a developing carrier, or the resulting mixture is developed into a developing carrier and the mixture is placed under conditions where the stimuli-responsive polymer agglutinates; the signal produced by the presence of the first binding substance or the second binding substance in the developing carrier is verified; and the presence of the detection target in the specimen is determined when the signal is different from that when the detection target is absent. The first affinity substance and the second affinity substance can bind to different positions of the detection target.

14 Claims, 8 Drawing Sheets

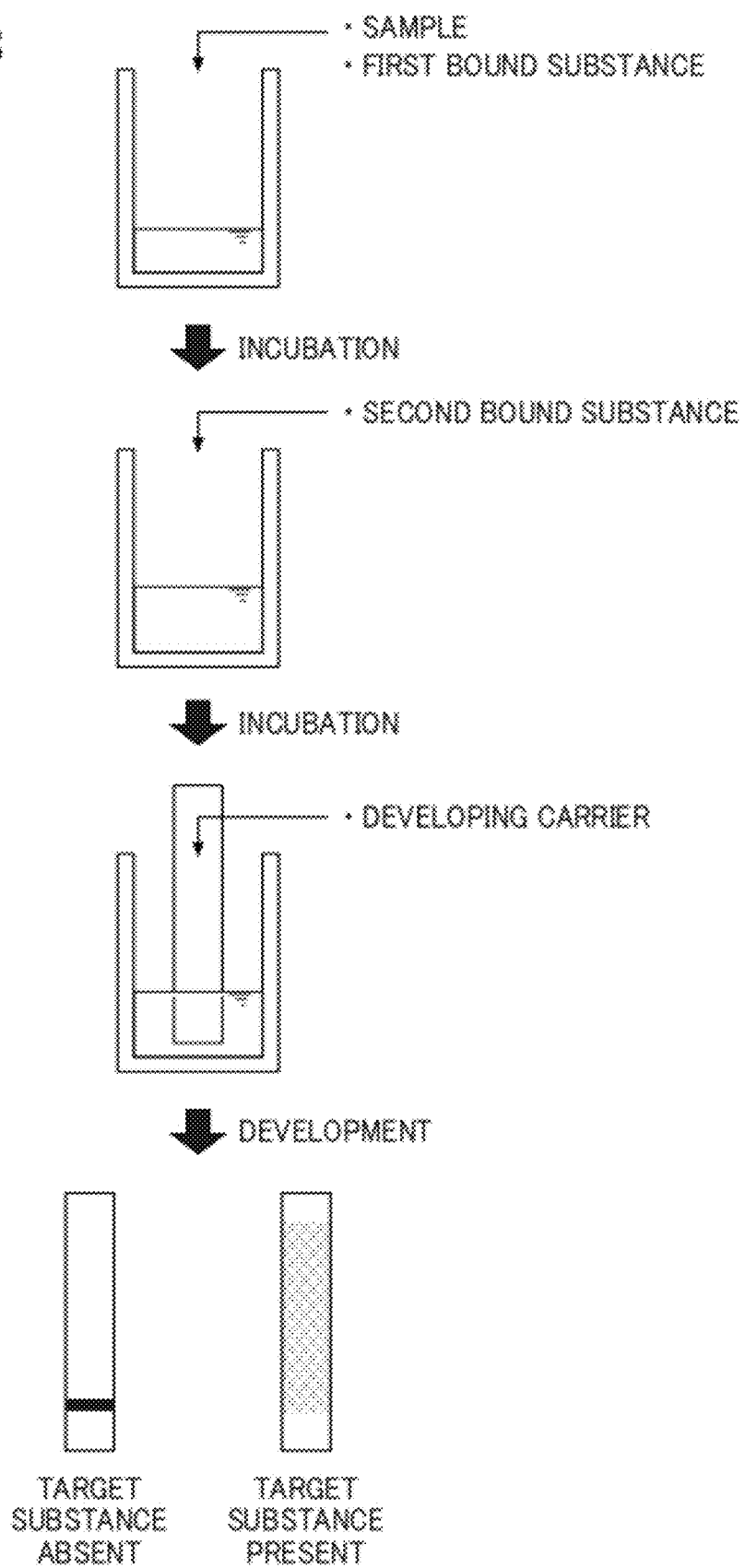

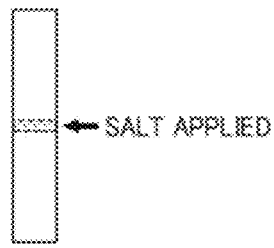
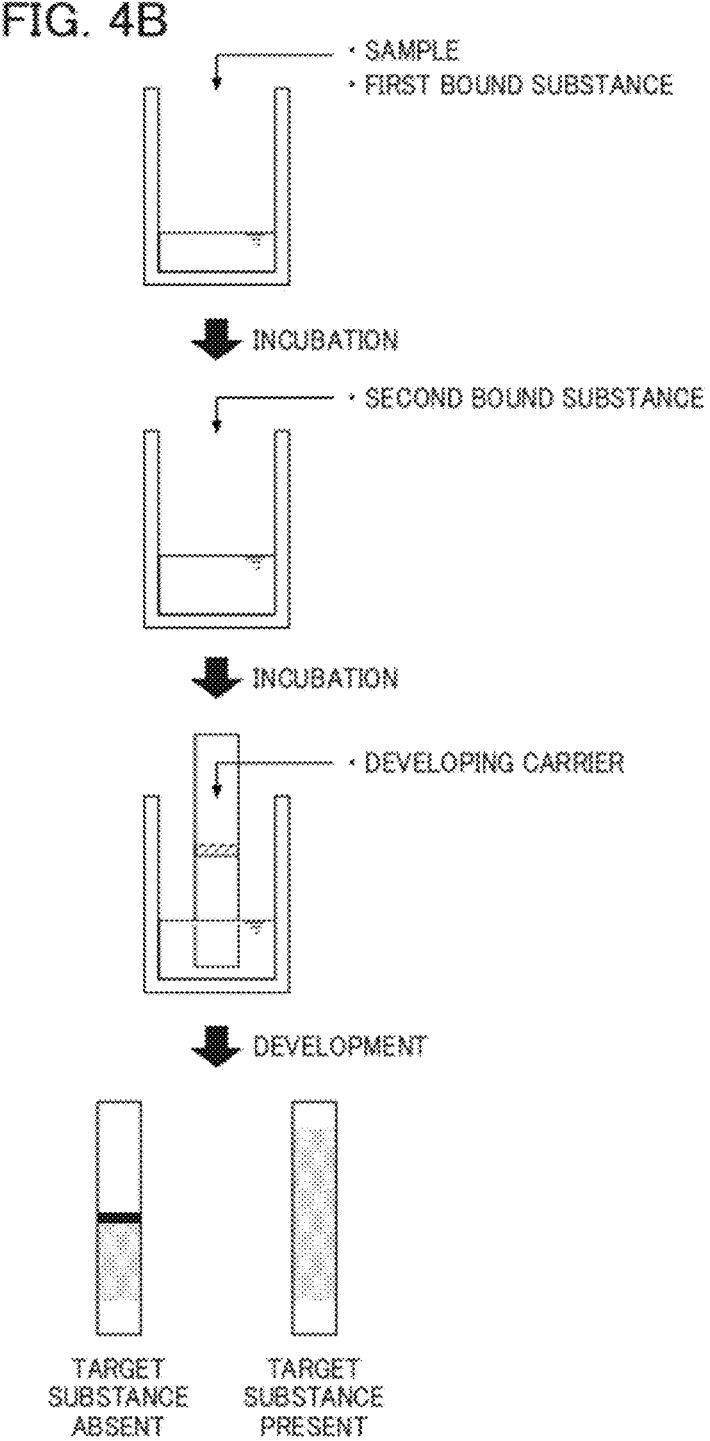

FIG. 5A
 ← COLORING OR LUMINESCENCE SUBSTANCE APPLIED
FIG. 5B
TARGET SUBSTANCE ABSENT
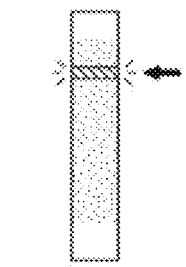
TARGET SUBSTANCE PRESENT
FIG. 6
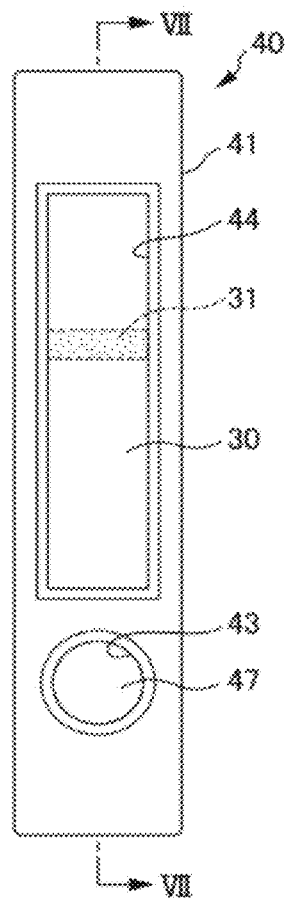

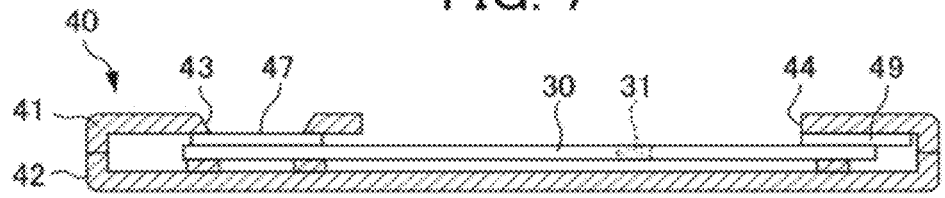
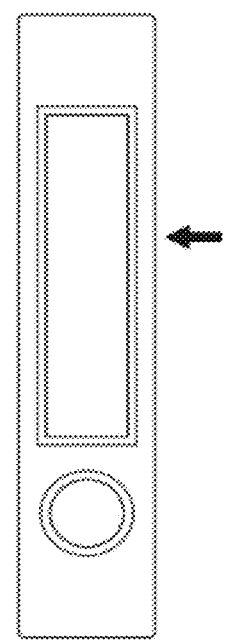
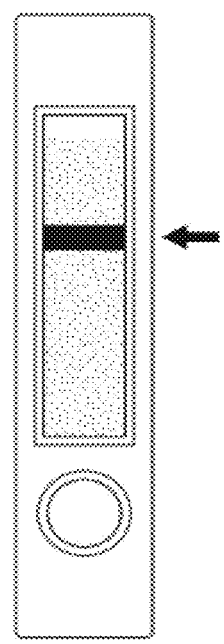

SAMPLE 1  SAMPLE 2

DETECTION METHOD AND QUANTIFICATION METHOD FOR TARGET SUBSTANCE

CROSS-REFERENCE TO RELATED APPLICATIONS

This application is a National Stage filing in the U.S. of International Application No. PCT/JP2010/058651, filed May 21, 2010, which is based on and claims the benefit of priority from Japanese Patent Application No. 2009-130958, filed on May 29, 2009, the entire contents of all of which are incorporated herein by reference.

FIELD OF THE INVENTION

The present invention relates to a method for detecting and quantifying a target substance.

BACKGROUND OF THE INVENTION

The latex aggregation method has long been used for detecting a target substance in a sample. In the latex aggregation method, in order to detect an antigen present in liquid such as a biological sample, the liquid and latex carrying an antibody or a fragment thereof that specifically binds to the target antigen are mixed, and the degree of latex aggregation is measured to detect or quantify the antigen (e.g., Japanese Published Examined Patent Application No. 558-11575, hereinafter referred to as Patent Document 1).

According to the latex aggregation method, aggregation of latex is facilitated by an antigen, which is added as a sample and cross-links a plurality of latex-bound antibodies. This simple procedure allows for convenient and rapid detection of an antigen. However, when the amount of the antigen is small, since it is difficult to generate cross-linking, a sufficient amount of latex cannot aggregate. Therefore, it has been difficult to detect a small amount of antigen.

Thus, methods utilizing an enzyme-substrate reaction, such as ELISA and CLEIA, are widely used. In these methods, for example, a primary antibody that binds specifically to an antigen is bound to an antigen, and a secondary antibody having an enzyme is bound to this primary antibody. Then, an enzyme substrate is added and the reactivity of a reaction catalyzed by the enzyme is measured to detect or quantify an antigen.

According to these methods, by using a luminescent reagent as a substrate, for example, the high detectability of a luminous reaction after adding the substrate allows detection of an extremely small amount of antigen.

However, the methods utilizing an enzyme-substrate reaction require a number of special reagents such as a secondary antibody and luminescent reagent, which make the operating cost high. Moreover, since the measuring process must be completed in an extremely short period of time to avoid color degradation (bleaching phenomenon) of the luminescent reagent, insufficiently accurate results are likely.

Meanwhile, these methods consist of a plurality of steps that make the operation complex, such as incubation of the specimen and each reagent, cleaning of the system, and detection of the luminous reaction. Each of these steps takes considerable time, and therefore these methods are not suitable for large-scale processing.

PATENT DOCUMENT

Patent Document 1

Japanese Examined Patent Application Publication No. S58-11575

SUMMARY OF THE INVENTION

Problems to be Solved by the Invention

Given this, the present inventors have developed a technique for detecting and quantifying a target substance using: a bound substance in which a substance containing a stimuli-responsive polymer binds to an affinity substance having affinity to the target substance; and a bound substance in which an electrically-charged substance binds to an affinity substance having affinity to the target substance (International Publication Pamphlet No. WO2008/001868). In this technique, a mixture of the abovementioned two bound substances and a sample is subjected to conditions to aggregate the stimuli-responsive polymer, and then, in a case where a degree of aggregation of the stimuli-responsive polymer is determined to be lowered as measured by turbidity measurement or the like, the target substance is determined to be present in the sample.

The abovementioned technique can be performed using only a substance including a stimuli-responsive polymer, an affinity substance and an electrically charged substance without particularly using any special reagent, and therefore is inexpensive and convenient. Additionally, the abovementioned technique only measures the degree of inhibition of aggregation and is not a system that utilizes a reaction catalyzed by an enzyme, and therefore can be conducted quickly.

However, in the abovementioned technique, precision equipment is often required for determination of the presence of the target substance and thus detection and quantification are preferably performed in a well-equipped environment such as an experimental laboratory. However, in a case of an environment pollution test and food inspection, detection and quantification are generally performed in a poorly equipped environment such as a non-laboratory environment, and therefore determination of the presence of the target substance is difficult.

The present invention was developed in view of the abovementioned situation and an object of the present invention is to provide a method for detecting and quantifying a target substance that allows for rapid, inexpensive, convenient and highly sensitive detection and quantification of a target substance in a variety of environments.

Means for Solving the Problems

The present inventors found that, by developing a mixture of two kinds of bound substances and a sample on a developing carrier, a signal resulting from the presence of the bound substance on the developing carrier is substantially different according to the presence or absence of a target substance, thus leading to the completion of the present invention. Specifically, the present invention provides the following.

In a first aspect of the present invention, a method for detecting a target substance in a sample includes steps of:

mixing a first bound substance in which a first substance containing a stimuli-responsive polymer binds to a first affinity substance having affinity to the target substance, a second bound substance in which a hydrophilic second substance binds to a second affinity substance having affinity to the target substance, and the sample; placing the mixture thus obtained under conditions to aggregate the stimuli-responsive polymer;

developing the mixture on a developing carrier or developing the mixture thus obtained on a developing carrier;

placing the mixture under conditions to aggregate the stimuli-responsive polymer; detecting a signal resulting from the presence of the first bound substance or the second bound substance on the developing carrier; and in a case where the signal is different from that detected in the absence of the target substance, determining that the target substance is present in the sample, in which the first affinity substance and the second affinity substance can bind to different sites of the target substance.

According to a second aspect of the present invention, in the method as described in the first aspect, the target substance is determined to be present in the sample in a case where intensity of the signal resulting from the presence of the first bound substance is lower than that in the absence of the target substance.

According to a third aspect of the present invention, in the method as described in the first aspect, the mixture is developed on the developing carrier after removing an aggregated substance of the first bound substance, and the target substance is determined to be present in the sample in a case where intensity of the signal resulting from the presence of the first bound substance is higher than that in the absence of the target substance.

In a fourth aspect of the present invention, a method for quantifying a target substance in a sample includes steps of:

mixing a first bound substance in which a first substance containing a stimuli-responsive polymer binds to a first affinity substance having affinity to the target substance, a second bound substance in which a hydrophilic second substance binds to a second affinity substance having affinity to the target substance, and the sample; placing the mixture thus obtained under conditions to aggregate the stimuli-responsive polymer;

developing the mixture on a developing carrier or developing the mixture thus obtained on a developing carrier;

placing the mixture under conditions to aggregate the stimuli-responsive polymer; determining intensity of a signal resulting from the presence of the first bound substance or the second bound substance on the developing carrier; and calculating an amount of the target substance in the sample based on a correlation equation between an amount of the target substance and intensity of the signal under the predetermined conditions, in which the first affinity substance and the second affinity substance can bind to different sites of the target substance.

According to a fifth aspect of the present invention, in the method as described in the fourth aspect, a signal resulting from the presence of an aggregate of the first bound substance is determined.

According to a sixth aspect of the present invention, in the method as described in the fourth aspect, the mixture is developed on the developing carrier after removing an aggregated substance of the first bound substance, and intensity of a signal resulting from the presence of the first bound substance is determined.

According to a seventh aspect of the present invention, in the method as described in any one of the first to sixth aspects, the first bound substance includes colored particles and the signal depends on a color resulting from the presence of the colored particles.

According to an eighth aspect of the present invention, in the method as described in any one of the first to seventh aspects, the first bound substance or the second bound substance includes a substance that produces color or luminescence on the developing carrier, the signal depends on a color or light resulting from the presence of the substance that produces color or luminescence.

In a ninth aspect of the present invention, a kit for at least any one of detection and quantification of a target substance includes:

a first bound substance in which a first substance containing a stimuli-responsive polymer binds to a first affinity substance having affinity to the target substance; a second bound substance in which a second substance, being hydrophilic, binds to a second affinity substance having affinity to the target substance; and a developing carrier for developing the bound substances.

According to a tenth aspect of the present invention, in the kit as described in the ninth aspect, the first bound substance includes colored particles.

According to an eleventh aspect of the present invention, in the kit as described in the ninth or tenth aspect, the first bound substance or the second bound substance includes a substance that produces color or luminescence on the developing carrier.

Effects of the Invention

According to the present invention, if a target substance is present, a first affinity substance and a second affinity substance bind to this binding target. Therefore, a stimuli-responsive polymer bound to the first affinity substance and a second substance bound to the second affinity substance are brought close to each other. Thus, the electrically charged moiety or the hydrophilic moiety is arranged in the vicinity of the stimuli-responsive polymer, whereby aggregation of the stimuli-responsive polymer, in response to stimulation, is inhibited. As a result, since a signal generated when the mixture is developed on the developing carrier is changed according to an amount of the target substance present, the target substance can be detected or quantified conveniently.

All of the abovementioned procedures can be conducted without particularly using any special reagent or instrument, and therefore can be conducted inexpensively and conveniently in a variety of environments. Additionally, the abovementioned procedure only determines a signal after development and is not a system that utilizes a reaction catalyzed by an enzyme, and therefore can be conducted quickly.

BRIEF DESCRIPTION OF THE DRAWINGS

FIG. 3 is a diagram showing steps of a method according to an embodiment of the present invention;

FIGS. 4 A-B are diagrams showing steps of a method according to another embodiment of the present invention;

FIGS. 5 A-B are diagrams showing steps of a method according to another embodiment of the present invention;

FIG. 6 is a plan view of a developing apparatus provided with a developing carrier used in a method according to another embodiment of the present invention;

FIG. 7 is a cross-sectional view taken along a line VII-VII of the developing apparatus of FIG. 6;

FIGS. 8 A-B are diagrams showing a change of the developing carrier of FIG. 6;

DETAILED DESCRIPTION OF THE INVENTION

Figure 1:
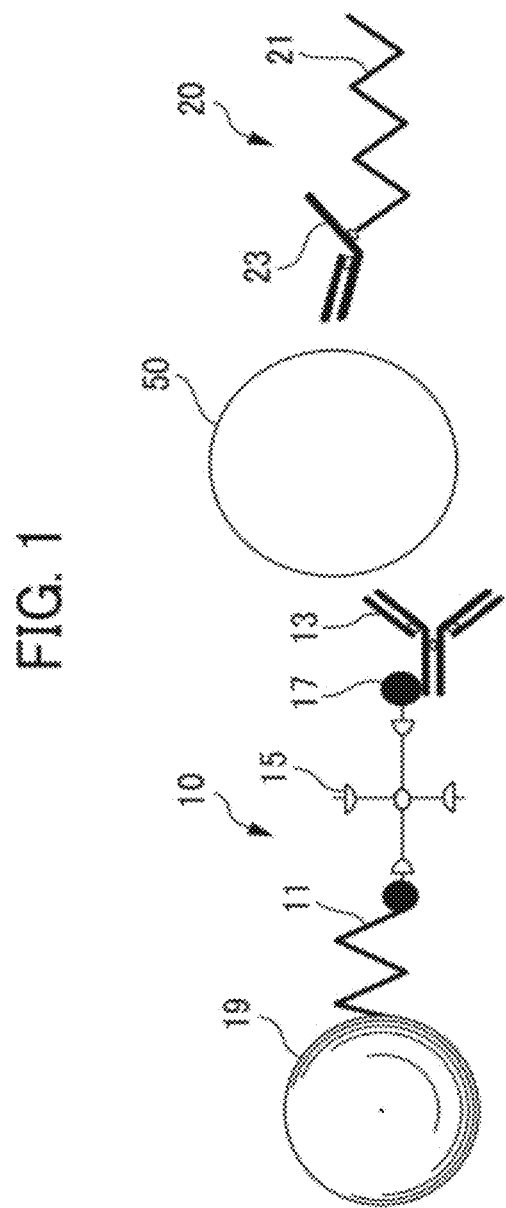
FIG. 1 is a schematic configuration diagram of the bound substance used in a method according to an embodiment of the present invention.

Below, an example of the present invention is explained with reference to diagrams.
Detection Method
Mixing and Aggregation In a method for detecting the target substance according to the present invention, firstly a bound substance and a sample are mixed, and the mixture thereof is subsequently subjected to conditions to aggregate the stimuli-responsive polymer. At least two kinds of bound substances are used therein. Among these, a first bound substance and a second bound substance, which are essential components, are described in detail.
First Bound Substance The first bound substance is a substance in which a first substance containing a stimuli-responsive polymer binds to a first affinity substance having affinity to the target substance.
First Substance The first substance used in the present invention contains a stimuli-responsive polymer which undergoes a structural change in response to an external stimulus, thereby being a polymer that can adjust the degree of aggregation and dispersion. The stimulus is not limited to a specific stimulus, temperature change, irradiation of light, addition of acid or base (change in pH) and electric field change can be used, for example.

Particularly, in the present invention, a temperature-responsive polymer, which is able to aggregate and disperse in response to temperature change, can be used as the stimuli-responsive polymer. The temperature-responsive polymer includes polymers which have a lower critical solution temperature (hereinafter referred to as LCST), and polymers which have an upper critical solution temperature (hereinafter referred to as UCST). For example, a polymer having a lower critical solution temperature with a LCST at 37° C. is completely dispersed in an aqueous solution with a temperature lower than LCST, and can be immediately aggregated by increasing the solution temperature to be higher than LCST. In addition, a polymer having an upper critical solution temperature with a UCST at 5° C. is completely dispersed in an aqueous solution with a temperature higher than UCST, and can be immediately aggregated by decreasing the solution temperature to be lower than UCST.

Polymers used in the present invention which have lower critical solution temperatures, include: polymers N-substituted (meth)acrylamide derivative such as N-n-propyl acrylamide, N-isopropyl acrylamide, N-ethyl acrylamide, N,N-dimethyl acrylamide, N-acryloyl pyrrolidine, N-acryloyl piperidine, N-acryloyl morpholine, N-n-propyl methacrylamide, N-isopropyl methacrylamide, N-ethyl methacrylamide, N,N-dimethyl methacrylamide, N-methacryloyl pyrrolidine, N-methacryloyl piperidine and N-methacryloyl morpholine; polyoxyethylene alkyl amine derivatives such as hydroxypropyl cellulose, polyvinyl alcohol partial acetal, polyvinylmethyl ether, (polyoxyethylene-polyoxypropylene) block copolymer, and polyoxyethylenelauryl amine; polyoxyethylenesorbitan ester derivatives such as polyoxyethylenesorbitanlaurate; (polyoxyethylenealkylphenyl ether) (meth)acrylates such as (polyoxyethylene nonylphenylether) acrylate, (polyoxyethyleneoctylphenylether)methacrylate; and polyoxyethylene(meth)acrylic ester derivatives such as (polyoxyethylene alkyl ether)(meth)acrylate of (polyoxyethylenelauryl ether)acrylate, (polyoxyethyleneoleyl ether) methacrylate. Furthermore, these polymers and copolymers having at least two unlike monomers of the above species can be used as well. In addition, a copolymer of N-isopropyl acrylamide and N-t-butyl acrylamide can also be used. When a polymer having (meth) acrylamide derivative is used, the polymer can be copolymerized with other copolymerizable monomers, as long as the polymer has a lower critical solution temperature. Particularly, in the present invention, polymers having at least one monomer selected from the group consisting of N-n-propyl acrylamide, N-isopropyl acrylamide, N-ethyl acrylamide, N,N-dimethylacrylamide, N-acryloyl pyrrolidine, N-acryloyl piperidine, N-acryloyl morpholine, N-n-propyl methacrylamide, N-isopropyl methacrylamide, N-ethyl methacrylamide, N,N-dimethyl methacrylamide, N-methacryloyl pyrrolidine, N-methacryloyl piperidine, and N-methacryloyl morpholine, or a copolymer of N-isopropyl acrylamide and N-t-butyl acrylamide are preferably used. In addition, an elastin-derived polypeptide having a repeating sequence of pentapolypeptide, as typified by Val-Pro-Gly-X-Gly (in which X is amino acid other than proline), can also be used.

Polymers having an upper critical solution temperature used in the present invention include polymers having at least one monomer selected from the group consisting of acryloyl glycineamide, acryloyl nipecotamide, acryloyl asparagineamide, and acryloyl glutamineamide, and the like. In addition, copolymers including at least two unlike monomers of these can be used as well. The abovementioned polymers can be copolymerized with other copolymerizable monomers such as acrylamide, acetyl acrylamide, biotinol acrylate, N-biotinyl-N'-methacryloyl trimethylene amide, acryloyl sarcosineamide, methacryl sarcosineamide, acryloyl methyluracil, etc. as long as the polymer has an upper critical solution temperature.

Additionally, in the present invention, a pH-responsive polymer which is able to aggregate and disperse by a change in pH can be used as the stimuli-responsive polymer. A pH at which a structural change of the pH-responsive polymer occurs is not limited to a particular pH, however, is preferably in the range of pH 4 to 10, more preferably in the range of pH 5 to 9, in order to prevent a decrease in the accuracy of detection/quantification due to denaturation and the like of the first bound substance, the second bound substance (described later) or the sample when the stimulus is applied.

The pH-responsive polymer includes polymers containing groups such as a carboxyl group, a phosphate group, a sulfonyl group, an amino group and the like as a functional group. More specifically, such pH-responsive polymer can be polymerized with monomers having a dissociable group, including: (meth)acrylic acid; maleic acid; styrenesulfonic acid; 2-acrylamide-2-methylpropanesulfonic acid; phosphoryl ethyl (meth)acrylate; amino ethyl methacrylate; aminopropyl (meth)acrylamide; and dimethylaminopropyl (meth)acrylamide. In addition, such pH-responsive polymer can be the abovementioned monomers having a dissociable group copolymerized with other vinyl monomers, by the degree that does not deteriorate the pH response: (meth)acrylic esters such as methyl (meth)acrylate, ethyl (meth)acrylate and butyl (meth) acrylate; vinyl esters such as vinyl acetate and vinyl propionate; vinyl compounds such as styrene, vinyl chloride, N-vinylpyrrolidone; and (meth) acrylamides.

Particle

The first substance can include a particle carrying a stimuli-responsive polymer and an affinity substance (described later). In order to change a signal on the developing carrier according to a degree of aggregation, the particle used herein is required to have an average particle diameter that is smaller than a pore diameter of a developing carrier (described later) when present as a discrete particle, and that is greater than the pore diameter of the developing carrier in an aggregated state; however, specific composition thereof is not particularly limited as long as the particle can carry the stimuli-responsive polymer and the affinity substance.

In a conventional latex aggregation method, since aggregation of latex due to the presence of a target substance must be detected, it is preferable that a particle has a large particle diameter in order to improve detection sensitivity. In contrast, in the method according to the present invention, as a particle has a smaller diameter, surface area per unit volume increases and aggregation of the stimuli-responsive polymer due to increase of binding of the target substance can be inhibited more effectively, therefore it is preferable that a particle has a small particle diameter. It should be noted that, it is required that the average particle diameter of the particle be set to be smaller than a pore diameter of a developing carrier in a non-aggregated state, and to be greater than the pore diameter of the developing carrier in an aggregated state. As described above, in a case of using a particle, the average particle diameter thereof can be accordingly set by considering effectiveness of inhibition of aggregation, mode of aggregation (particularly change in diameter), pore diameter of the developing carrier and the like. Generally, a lower limit of the average particle diameter thereof is preferably 0.001 um, more preferably 0.010 μm, and most preferably 0.1 μm. An upper limit is preferably 0.5 μm, more preferably 0.3 μm, and most preferably 0.2 μm.

The particle is preferably a colored particle that generates a signal depending on a color when developed on a developing carrier, the signal being easily detected or measured. The colored particle is not particularly limited and can be a metallic colloid particle (e.g. a gold colloid particle), a homogeneous spherical particle and the like consisting of a synthetic polymer such as polystylene latex, or a natural polymer such as gelatin. However, the first bound substance can be used not only for the method according to the present invention, but also for a detection method disclosed in International Publication Pamphlet No. WO 2008/001868. In the latter case, detection sensitivity can be improved by separating an aggregate by applying a magnetic force (for details, see International Publication Pamphlet No. WO 2008/001868). Given this, in order to increase versatility, the particle preferably includes a magnetic material, which can be constituted of a multivalent alcohol and magnetite.

Any multivalent alcohol can be used without limitation, provided that it has at least two hydroxyl groups in constitutional units and can bind to an iron ion, for example, dextran, polyvinyl alcohol, mannitol, sorbitol, and cyclodextrin. For example, Japanese Unexamined Patent Application No. 2005-82538 discloses a method for manufacturing particulate magnetic material using dextran. Alternatively, a compound such as glycidyl methacrylate polymer, which has an epoxy group and forms a multivalent alcohol structure after ring opening, can be used as well.

The First Affinity Substance

The first affinity substance may be a monoclonal antibody which recognizes the different antigenic determinants of the target substance. The antibody used herein can be any type of immunoglobulin molecule, for example an immunoglobulin molecule fragment which has an antigen binding site such as Fab. In addition, the antibody can be a monoclonal antibody or a polyclonal antibody.

Preparation of First Bound Substance

The first bound substance is prepared by binding the first substance and the first affinity substance. Though, the binding method is not limited to a particular method; for example, substances having affinity to each other (e.g., avidin and biotin, glutathione and glutathione S-transferase) are bound to the first substance (for example, a stimuli-responsive polymer moiety) and to the first affinity substance (for example, the first antibody), and the first substance and the first affinity substance are bound to each other via these substances.

Specifically, as described in the International Publication No. WO 01/009141, biotin can be bound to the stimuli-responsive polymer by binding biotin or other affinity substances to a polymerizing functional group such as methacryl or acryl to produce an addition polymerizable monomer, which further copolymerizes with other monomers. In addition, avidin or the other affinity substances can be bound to the first affinity substance by a common method. Then, by mixing a biotin-bound stimuli-responsive polymer and an avidin-bound first affinity substance, the first affinity substance and the stimuli-responsive polymer are bound to each other via binding between avidin and biotin.

As an alternative, during manufacture of a polymer, a monomer having functional groups such as a carboxyl group, an amino group or an epoxy group can be copolymerized with another monomer, then an antibody affinity substance (e.g., melon gel, protein A, protein G, etc.) can be bound to the polymer via the functional group according to a method known in the art. The antibody affinity substance thus obtained can be bound to the first antibody, to obtain a first bound substance in which the stimuli-responsive polymer binds to the first antibody of the target antigen.

Alternatively, during manufacture of a polymer, a monomer having functional groups such as a carboxyl group, an amino group or an epoxy group can be copolymerized with another monomer, then the first antibody for the target antigen can be bound directly to these functional groups according to a commonly known method.

Alternatively, the first affinity substance and the stimuli-responsive polymer can be bound to the particulate magnetic material.

The first bound substance can be purified by subjecting the first substance containing the stimuli-responsive polymer to a condition where the stimuli-responsive polymer aggregates, followed by separating the aggregated polymer by centrifugation. The first bound substance can also be purified by binding the particulate magnetic material, and then the first affinity substance to the stimuli-responsive polymer, followed by subjecting to conditions to aggregate the stimuli-responsive polymer and collecting the magnetic material by applying a magnetic force.

The particulate magnetic material and the stimuli-responsive polymer can be bound by a method well-known in the art, such as a method of binding via a reactive functional group, or a method to graft polymerize from an active hydrogen in a multivalent alcohol or from a polymerizable unsaturated bond introduced to a multivalent alcohol itself in the magnetic substance (See, ADV. Polym. Sci., Vol. 4, p. 111, 1965; J. Polymer Sci., Part-A, 3, p 1031, 1965).

Second Bound Substance

In the method according to the present invention, in addition to the first bound substance, a second bound substance is used in which a hydrophilic second substance binds to a second affinity substance having affinity to the target substance. This can improve detection sensitivity.

Second Substance

The hydrophilic second substance is, for example, an electrically charged polymer compound, preferably a polyanion or polycation. The polyanion indicates a substance which has a plurality of anion groups, and the polycation indicates a substance which has a plurality of cation groups. Examples of the polyanion include nucleic acids such as DNA and RNA. These nucleic acids have the property of a polyanion because they have a plurality of phosphodiester groups along the backbone of the nucleic acids. In addition, the polyanion includes a polypeptide containing many carboxyl groups (polypeptide consisting of amino acids such as glutamic acid and aspartic acid), polymers including polyacrylic acid, polymethacrylic acid, polysulfonic acid, acrylic acid or methacrylic acid as a polymerization component, and polysaccharides such as carboxymethylcellulose, hyaluronic acid and heparin. On the other hand, examples of the polycation include polylysine, polyarginine, polyornithine, polyalkylamine, polyethyleneimine, and polypropyl ethyleneimine, and the like. The number of functional groups of the polyanion (carboxyl group) or the polycation (amino group) is preferably at least 25. In addition, a latex particle having a carboxyl group can also be exemplified.

The hydrophilic second substance is, for example, a water-soluble polymer compound such as: polymers containing an ether bond such as polyethylene glycol, polypropylene glycol, polyethylene oxide and polypropylene oxide; polymers containing an alcoholic hydroxyl group such as polyvinyl alcohol; water-soluble polysaccharides such as dextran, cyclodextrin, agarose and hydroxypropylcellulose; and polypeptide containing neutral amino acid.

Such hydrophilic substances can have a functional group and the like in the polymer chain or at the end of the polymer chain to bind the second affinity substance. In addition, the hydrophilic second substance can be either one substance used singly or multiple substances used in mixture.

Second Affinity Substance

The second affinity substance is a substance which can bind to different sites of the same target substance as the first affinity substance. For example, the first affinity substance and the second affinity substance may be a monoclonal antibody recognizing the different antigenic determinants of the target substance.

Preparation Method

The second bound substance is prepared by binding directly or indirectly the second substance and the second affinity substance. The binding method is not limited to a particular method; however, for example, substances having affinity to each other (e.g., avidin and biotin, glutathione and glutathione S-transferase) are bound to both of the second substance and the second affinity substance (for example, the second antibody), and the second substance and the second affinity substance are indirectly bound to each other via the affinity substances.

When the second substance and the second affinity substance are directly bound, they can be bound via a functional group, for example, when using a functional group, maleimide-thiol coupling as in the method of Ghosh et al., (Ghosh et al.: Bioconjugate Chem., 1, 71-76, 1990) can be used. Specifically, the following two methods can be adopted.

According to a first method, a mercapto group (sulfhydryl group) is introduced to the 5' end of the nucleic acid, and a maleimide group is introduced to the antibody by reacting 6-maleimide hexanoic acid succinimide ester (e.g., EMCS (trade name) manufactured by DOJINDO LABORATORIES) with the antibody. Next, the abovementioned two substances are bound to each other via the mercapto group and the maleimide group.

According to a second method, a mercapto group is introduced to the 5' end of the nucleic acid, in a similar way to the first method. Then, the mercapto group is introduced to the antibody while N,N-1,2-phenylene di-maleimide, a homo bi-functional reagent, reacts with this mercapto group to introduce a maleimide group to the 5' end of the nucleic acid. Next, the abovementioned two substances are bound to each other via the mercapto group and the maleimide group.

Other methods known in the art to introduce nucleic acid to a protein include methods, for example, described in Nucleic Acids Research Vol. 15, p. 5275 (1987) and Nucleic Acid Research Vol. 16, p. 3671 (1988). These techniques can be applied for binding nucleic acid and antibody.

According to Nucleic Acids Research Vol. 16, p. 3671 (1988), an oligonucleotide reacts with cystamine, carbodiimide, and 1-methylimidazole to introduce a mercapto group to the hydroxyl group at the 5' end of the oligonucleotide. After purifying the oligonucleotide, to which the mercapto group is introduced, the oligonucleotide is reduced by using dithiothreitol. Subsequently, by adding 2,2'-dipyridyl disulfide, a pyridyl group is introduced to the 5' end of the oligonucleotide via disulfide bond. On the other hand, regarding the protein, a mercapto group is introduced by reacting iminothiolane. The oligonucleotide to which the pyridyl disulfide is introduced and the protein to which mercapto group is introduced are mixed to react the pyridyl group and mercapto group specifically in order to bind the protein and the oligonucleotide.

According to Nucleic Acids Research Vol. 15, p. 5275 (1987), an amino group is introduced to the 3' end of the oligonucleotide, and reacted with dithio-bis-propionic acid-N-hydroxysuccinimide ester (abbreviated name: dithio-bis-propionyl-NHS), which is a homo bi-functional reagent. After the reaction, dithiothreitol is added to reduce the disulfide bond in the dithio-bis-propionyl-NHS molecule, then a mercapto group is introduced to the 3' end of the oligonucleotide. For treatment of the protein, a hetero bi-functional cross linking agent, as described in Japanese Unexamined Patent Application No. H5-48100, is used. First, the protein reacts with the hetero bi-functional cross-linking agent having a first reactive group (succinimide group) that can react with a functional group (e.g., amino group) in the protein and a second reactive group (e.g. maleimide group) that can react with mercapto group. Then, the second reactive group is introduced to the protein to obtain a protein reagent activated in advance. The resulting protein reagent is bound covalently to the mercapto group of thiolized polynucleotide.

When using a polyanion and polycation other than the nucleic acid, by introducing a mercapto group to the ends or the other parts thereof, a second bound substance can be prepared in a similar way to the above.

The steps of the detection method are described again hereinafter. By subjecting a mixture of the abovementioned two bound substances and the sample to the conditions to aggregate the stimuli-responsive polymer, in a case where the target substance is present, aggregation of the stimuli-responsive polymer is inhibited by the electrically charged moiety or the hydrophilic moiety of the target substance, and the stimuli-responsive polymer disperses. On the other hand, in a case where the target substance is not present, the stimuli-responsive polymer aggregates since aggregation thereof is not inhibited. It should be noted that the first bound substance, the second bound substance, and the sample can be either mixed at once or mixed individually.

This phenomenon is described with reference to FIGS. 1 and 2.

As shown in FIG. 1, a first bound substance 10 contains a stimuli-responsive polymer 11, and the stimuli-responsive polymer 11 is bound to a first antibody 13 for a target substance 50 via avidin 15 and biotin 17. Furthermore, the first bound substance 10 includes particulate magnetic material, and the stimuli-responsive polymer 11 as the first substance is bound to the surface of this magnetic material 19. On the other hand, in a second bound substance 20, a hydrophilic second substance 21 is bound to a second antibody 23 for the target substance 50. Then, the first antibody 13 and second antibody 23 can be bound to the same target substance 50, since the antibodies can be bound to different sites of the target substance 50. The second bound substance 20 can be brought close to the magnetic material 19 via the target substance 50 and the stimuli-responsive polymer 11, and the second substance 21 is located in the vicinity of the magnetic material 19.

Figure 2A:
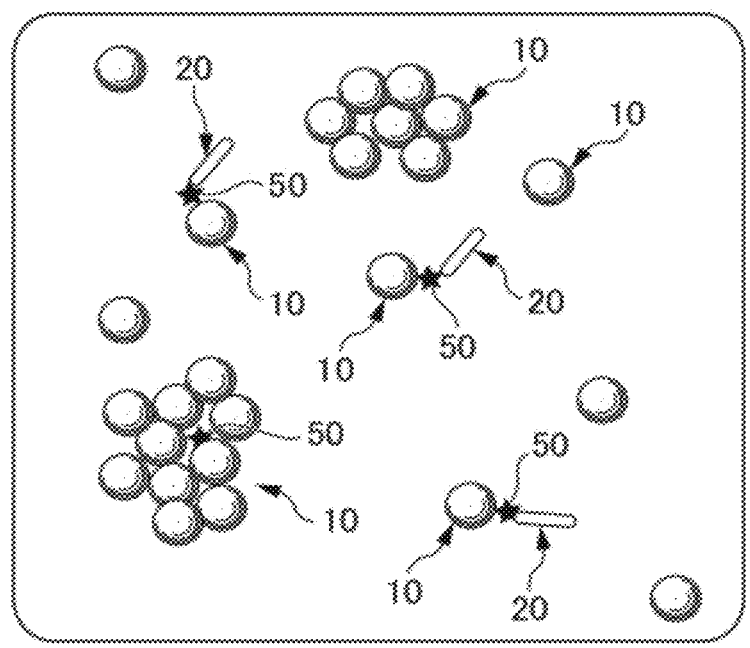
FIGS. 2 A-B are schematic views showing a usage state of the bound substance according to the embodiment of the present invention.
Figure 2B:
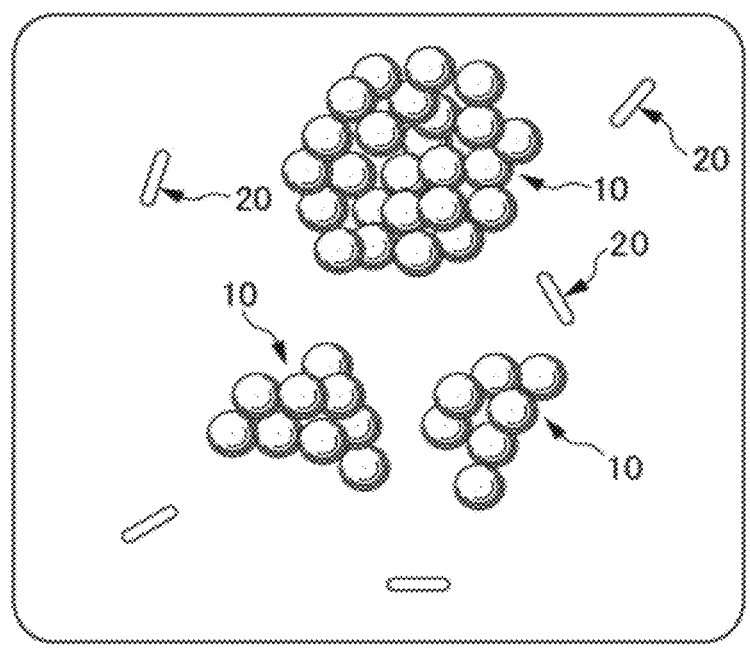

As shown FIG. 2, by subjecting a mixture of the first bound substance 10, the second substance 20, and the sample to the predetermined conditions, in a case where the target substance is present, aggregation of the stimuli-responsive polymer is inhibited by the electrically charged moiety or the hydrophilic moiety of the second bound substance 20, and the stimuli-responsive polymer disperses (FIG. 2A). On the other hand, in a case where the target substance 50 is not present, the stimuli-responsive polymer 11 aggregates since aggregation thereof is not inhibited (FIG. 2B). It should be noted that, although the electrically charged moiety or the hydrophilic moiety of the second bound substance 20 is located in the vicinity of the magnetic material 19 in the present embodiment, the present invention is not limited thereto. An electrically charged moiety or a hydrophilic moiety of the target substance can also be located in the vicinity of the magnetic material 19.

To aggregate the stimuli-responsive polymer 11, for example, in cases where a temperature-responsive polymer is used, a vessel containing the mixture can be moved to an incubator at an aggregation temperature of the temperature-responsive polymer. There are two types of temperature-responsive polymers: a polymer having an upper critical solution temperature (may hereinafter be abbreviated as UCST); and a polymer having a lower critical solution temperature (may hereinafter be abbreviated as LCST). For example, in a case where a polymer having a lower critical solution temperature with a LCST at 37° C. is used, the temperature-responsive polymer can be aggregated by placing the vessel containing the mixture in an incubator of no less than 37° C. In a case where a polymer having an upper critical solution temperature with a UCST at 5° C. is used, the temperature-responsive polymer can be aggregated by placing the vessel containing the mixture in an incubator of no greater than 5° C.

In addition, LCST is known to decrease as salt concentration in a periphery of the temperature-responsive polymer increases. Therefore, by adding a salt (for example, NaCl) of a predetermined concentration to a solution in which the temperature responsive polymer is dispersed at a certain temperature, it is possible to aggregate the temperature responsive polymer at a constant temperature.

As a salt used in the present invention: sulfate such as lithium sulfate, sodium sulfate, potassium sulfate, magnesium sulfate, ammonium sulfate and the like; halide such as sodium chloride, potassium chloride, magnesium chloride, calcium chloride, barium chloride; nitrate such as magnesium nitrate and calcium nitrate; thiocyanate such as potassium thiocyanate; carbonate such as sodium carbonate and potassium carbonate; borate; and phosphate can be exemplified. These salts can be used either singly or in combination of at least two thereof. In addition, an organic acid salt and the like such as: a sodium salt of a monocarbonic acid such as sodium acetate; a sodium salt of a dicarboxylic acid such as sodium aspartate, sodium glutamate, sodium iminodiacetate, sodium maleate, sodium malonate, sodium oxalate, disodium succinate or sodium tartrate; a sodium salt of a tricarboxylic acid such as disodium citrate; and a sodium salt of a tetracarboxylic acid such as disodium ethylenediaminetetraacetate can also be exemplified. Furthermore, an organic acid salt and the like such as a potassium salt thereof can also be used. These salts can be used either singly or in combination of at least two thereof.

For aggregating the temperature-responsive polymer, for example, an aqueous solution of a salt can be added to obtain a desired salt concentration. An amount of salt necessary to aggregate the temperature-responsive polymer depends on a type of salt, a temperature of an aqueous solution, a type of the temperature-responsive polymer, and a concentration of the temperature responsive polymer; however, a final concentration in an aqueous solution is approximately in a range of 50 mM to 5 M, and preferably in a range of 100 to 1000 mM.

In addition, in a case where a pH-responsive polymer is used, an acid solution or an alkaline solution can be added to the vessel containing the mixture. Specifically, to a vessel containing a dispersed mixture with a pH in the range in which a structural change of the pH-responsive polymer does not occur, an acid solution or an alkaline solution can be added to change the pH of the dispersed mixture to the range in which a structural change of the pH-responsive polymer occurs. For example, in a case where a pH-responsive polymer, which aggregates at a pH of no greater than 5 and disperses at a pH greater than 5, is used, an acid solution can be added to the vessel containing the mixture that is dispersed at a pH greater than 5, to lower the pH to be no greater than 5. In addition, in a case where a pH-responsive polymer, which aggregates at a pH of no less than 10 and disperses at a pH of less than 10, is used, an alkaline solution can be added to the vessel containing the mixture that is dispersed at a pH less than 10, to raise the pH to be no less than 10. A pH at which a structural change of the pH-responsive polymer occurs is not limited to a particular pH; however, is preferably in the range of pH 4 to 10, more preferably in the range of pH 5 to 9. More specifically, a polypeptide containing many carboxyl groups (polypeptide consisting of amino acids such as glutamic acid and aspartic acid), polyacrylic acid, polymethacrylic acid, polymers including acrylic acid or methacrylic acid as a polymerization component, polysaccharides such as carboxymethylcellulose, hyaluronic acid and heparin, polylysine, polyarginine, polyornithine, polyalkylamine, polyethylenimine, poly(propylethylenimine) and the like can be exemplified.

Furthermore, in a case where a light-responsive polymer is used, the vessel containing the mixture can be irradiated with light having a wavelength that can aggregate the polymer. The preferred type of light depends on the type and structure of a light responsive functional group contained in the light-responsive polymer, however, generally ultraviolet radiation or visible radiation with a wavelength in the range of 190 to 800 nm can preferably be used. A luminous intensity thereof is preferably in the range of 0.1 to 1000 mW/cm$^2$. For improved measurement accuracy, the light-responsive polymer is preferably not dispersed, in other words is preferably aggregated, by the irradiation of light for the measurement of turbidity. In a case where a light-responsive polymer is used which disperses upon irradiation of light used for the measurement of turbidity, accuracy of the measurement can be improved by shortening irradiation time. More specifically, a polymer and the like containing a photoresponsive functional group such as azobenzene, spirobenzopyran and spirobenzothiopyran can be exemplified.

By subjecting a mixture of the first bound substance 10, the second substance 20, and the sample to such conditions, in a case where the target substance is present, aggregation of the stimuli-responsive polymer is inhibited by the electrical charged moiety or the hydrophilic moiety of the second bound substance 20, and the stimuli-responsive polymer disperses (FIG. 2A). On the other hand, in a case where the target substance 50 is not present, the stimuli-responsive polymer 11 aggregates since aggregation thereof is not inhibited (FIG. 2B).

Note that aggregation of temperature-responsive polymer can be simultaneously with or after binding to the first bound substance and the second bound substance; the latter should be preferred due to shorter processing time.

Here, the lower critical solution temperature is determined as follows. To begin with, a sample is added to a cell of an absorptiometer, and heated at a rate of 1° C./min. During this period, the change in transmittance at 550 nm is recorded. Transmittance is 100% when the polymer is dissolved to be transparent, and 0% when completely aggregated. LCST is defined by determining the temperature where the transmittance is 50%.

In addition, the upper critical solution temperature is determined as follows. The sample is cooled at a rate of 1° C./min. and the change in transmittance at 550 nm is recorded in the same way as in the case of the lower critical solution temperature. Transmittance is 100% when the polymer is dissolved to be transparent, and 0% when completely aggregated. UCST is defined by determining the temperature where the transmittance is 50%.

Determination

A mixture of the sample and the bound substances is developed on the developing carrier. A signal resulting from the presence of the bound substance on the developing carrier is detected, and in a case where the signal is different from that detected in the absence of the target substance, it is determined that the target substance is present in the sample. In other words, as shown in FIG. 2, since a state of aggregation in each mixture is different according to the presence or absence of the target substance, a mode of development of each mixture is different. Given this, the presence of the target substance in the sample can be determined in a case where a signal is detected that is different from that detected in the absence of the target substance. As described above, the determination can be made only by determining a signal on the developing carrier, without particularly using any special reagent or instrument, and therefore detection can be conducted inexpensively and conveniently in a variety of environments.

Note that, as described later, the mixture can be subjected to conditions to aggregate the stimuli-responsive polymer either before development (the mixture is developed after being subjected to conditions to aggregate) or simultaneously with development (the mixture is subjected to conditions to aggregate while being developed).

Developing Carrier

The developing carrier used in the method of the present invention is not particularly limited as long as the carrier can develop particles in a solution and can be a conventionally known chromatographic carrier. More specifically, a perforated membrane of a three-dimensional structure such as a nylon membrane and nitrocellulose membrane, which can be either synthetic or natural polymeric membrane, can be exemplified. However, since the developing carrier is required to have a pore diameter greater than an average particle diameter of the abovementioned particle and smaller than a diameter of an aggregate, a pore diameter of the developing carrier is preferably 0.01 μm to 0.5 μm approximately, which is versatile and can be used for various particles.

A specific procedure of the development and determination is not particularly limited and can be arbitrary. A preferable procedure is described hereinafter.

FIG. 3 is a diagram showing steps of a method according to an embodiment of the present invention. In the present embodiment, the sample and the first bound substance are mixed and incubated in the abovementioned conditions, and the second bound substance is mixed thereinto and incubated in the abovementioned conditions. In the present embodiment, the conditions to aggregate the stimuli-responsive polymer are already met in this step.

Thereafter, the developing carrier is immersed in the mixture up to a predetermined height from a bottom end thereof, and the mixture is developed in this state. Subsequently, in a case where the target substance is not present in the sample, a large amount of aggregate is formed in the mixture and concentrated at a meniscus since a diameter of the aggregate is larger than a pore diameter. As a result, a colored band (an example of the signal) resulting from the presence of a bound substance (generally particles) in the aggregate is detected. On the contrary, in a case where the target substance is present in the sample, an amount of the aggregate is significantly reduced depending on the amount of the target substance present and therefore non-aggregated body smaller than the pore diameter moves on the developing carrier. As a result, the colored band resulting from the presence of the aggregate is not detected or becomes pale and a colored area (an example of the signal) resulting from the presence of a bound substance (generally particles) in the non-aggregated body is detected extensively.

Therefore, in a case where intensity of the signal (density in the colored area) resulting from the presence of the aggregate is lower than in the absence of the target substance, the target substance can be determined to be present in the sample. In addition, in the present embodiment, the target substance can be determined to be present in the sample also in a case where a position of the colored area is different from that in the absence of the target substance.

FIG. 4 is a diagram showing steps of a method according to another embodiment of the present invention. In the present embodiment, as shown in FIG. 4a, a salt (for example, NaCl) in an effective amount to aggregate the stimuli-responsive polymer (particularly a polymer having LCST) at room temperature is disposed at a position away from a bottom end of the developing carrier (which is shown for the sake of clarity, and can be visually unrecognizable in practice). And development is started without subjecting the mixture to conditions to aggregate (for example, placing the mixture at a temperature lower than LCST of the stimuli-responsive polymer).

In a case where the target substance is not present in the sample, the mixture moves to a position where the salt is disposed, where the mixture concentrates as a result of aggregating and being immobile. On the contrary, in a case where the target substance is present in the sample, the mixture passes through the position where the salt is disposed and moves further, since aggregation is inhibited. As a result, the colored band resulting from the presence of the aggregate is not detected or becomes obscure and a colored area (an example of the signal) resulting from the presence of a bound substance (generally particles) in the non-aggregated body is detected extensively.

Therefore, in a case where intensity of the signal (density in the colored area) resulting from the presence of the aggregate is lower than in the absence of the target substance, the target substance can be determined to be present in the sample. In addition, in the present embodiment, the target substance can be determined to be present in the sample also in a case where a range of a colored area resulting from the presence of the bound substance (generally particles) in the non-aggregated body is different from that in the absence of the target substance.

In the above embodiment, since the colored band is detected at a meniscus, the colored band may be blurred in an environment where it is difficult to keep a liquid level constant; however, in the present embodiment, since the colored band is detected at a position where the salt is disposed, the colored band can be made clear regardless of liquid level. This effect is particularly important in a case of detection in an environment such as a non-laboratory environment.

It should be noted that the position where the salt is disposed is not particularly limited and can be an arbitrary position higher than a bottom end of the developing carrier. However, it is preferable to dispose the salt in the vicinity of a center of the developing carrier, for obtaining the same signal regardless of a direction of the developing carrier (in other words, regardless of whether both end portions thereof are directed upward or downward). This effect is also particularly important in a case of detection in an environment such as a non-laboratory environment. In addition, by providing a marker and the like showing a direction of the developing carrier, a degree of freedom of the position where the salt is disposed can be increased.

Although a salt is disposed in the developing carrier in the present embodiment, the present invention is not particularly limited thereto as long as a condition for aggregating the stimuli-responsive polymer can be provided. More specifically, only a predetermined site in the developing carrier can be set to a temperature at which aggregation occurs, can have disposed therein an acid or a base for making a pH at which aggregation occurs, or can be irradiated with light.

FIG. 5 is a diagram showing steps of a method according to another embodiment of the present invention. In the present embodiment, as shown in FIG. 5a, a substance that produces color or luminescence on a developing carrier in the presence of the bound substance is disposed at a position away from a bottom end of the developing carrier (which is shown for the sake of clarity, and can be visually unrecognizable in practice). By performing the development using such a developing carrier in the same procedure as in FIG. 3, in a case where the target substance is present in the sample, a non-aggregated body smaller than the pore diameter moves on the developing carrier to a position of the substance that produces color or luminescence, where color formation or luminescence (an example of the signal) is detected as shown in FIG. 5b. On the contrary, in a case where the target substance is not present in the sample, a large amount of aggregate is formed in the mixture and therefore color formation or luminescence is difficult to be detected. According to the present mode, sensitivity and precision of detection can be further improved by accordingly selecting intensity of color formation or luminescence. In the present mode, color formation or luminescence corresponds to the signal.

The substance that produces color or luminescence can be accordingly selected from conventionally known substances. As the substance that produces color, a substance having an absorption band in a visible region can be exemplified, such as triazine and 1,10-phenanthroline. As the luminescence substance, fluorescent or chemiluminescence substance can be exemplified, such as luminol and luciferase. The substance that produces color is preferred to the substance that produces luminescence, for being visible to the naked eye and not requiring a light irradiation apparatus and the like; however, the present invention is not limited thereto. In addition, in a case where a magnetic material is used, magnetic quantity, which corresponds to the signal in this case, can be measured.

It should be noted that, in the mode shown in FIG. 5, by configuring the bound substance to be colored, a colored area resulting from the presence of the aggregate can be seen at a position corresponding to a meniscus, in a case where the target substance is not present in the sample. As described above, a single signal or a plurality of signals can be accordingly selected.

FIG. 6 is a plan view of a developing apparatus 40 provided with a developing carrier 30 used in a method according to another embodiment of the present invention. FIG. 7 is a cross-sectional view taken along a line VII-VII of the developing apparatus 40 of FIG. 6.

As shown in FIG. 7, in a developing apparatus 40, a filter 47 is disposed in a first end (a bottom end in FIG. 6 and a left end in FIG. 7) of the developing carrier 30 that is arranged horizontally, and a substance that produces color or luminescence on the developing carrier 30 in the presence of the bound substance is disposed at a position 31 away from the first end. In addition, a liquid absorbent body 49 is in contact with a second end of the developing carrier 30.

The filter 47 can be composed of either the same or different material as the developing carrier 30; however, the filter 47 is required to let through a non-aggregated body but not an aggregate, in other words, to have a pore diameter greater than the average particle diameter of the abovementioned discrete particle and smaller than a diameter of an aggregate. In addition, the liquid absorbent body 49 is not particularly limited as long as a solvent in the mixture can be absorbed.

In this state, the developing carrier 30, the filter 47 and the liquid absorbent body 49 are supported by an upper supporting member 41 and a lower supporting member 42, where the filter 47 is exposed through a feed opening portion 43 and the position 31 can be visually recognizable through a window portion 44. It should be noted that a mode for supporting is not particularly limited; however, the upper supporting member 41 and the lower supporting member 42 are preferably detachable for reuse of the upper supporting member 41 and the lower supporting member 42.

By using the developing apparatus 40, the filter 47 is loaded with a mixture prepared by the same procedure as in FIG. 3. The mixture is thus developed on the developing carrier after an aggregate is removed by the filter 47. Accordingly, in a case where the target substance is present in the sample, a large amount of non-aggregated body passes through the filter 47 and moves on the developing carrier to the position 31. As a result, color formation or luminescence is detected at the position 31. On the contrary, in a case where the target substance is not present in the sample, a large amount of aggregate formed in the mixture remains on the filter 47 while there is an extremely small amount of or no non-aggregated body that can pass through the filter 47, therefore color formation or luminescence is difficult to be detected at the position 31.

Therefore, in a case where intensity of the signal (here, color formation or luminescence) resulting from the presence of the aggregate is higher than in the absence of the target substance, the target substance can be determined to be present in the sample. The present embodiment is, unlike the abovementioned embodiment, preferable as being suitable for an environment without a supporting table and an environment in which air moves due to wind and the like, such as non-laboratory environment, since a restriction of supporting the developing carrier during development at the same position with respect to the mixture is small.

Quantitative Method

In a quantitative method according to the present invention, to begin with a first bound substance, a second bound substance and a sample are mixed, and the mixture thereof is subsequently subjected to predetermined conditions to aggregate the stimuli-responsive polymer. Then, the mixture is developed on the developing carrier, intensity of a signal resulting from a bound substance on the developing carrier is measured, and the amount of a target substance in the sample is calculated based on a correlation equation between the amount of the target substance and the intensity of the signal under the predetermined condition. An explanation is omitted for a procedure for development, which is similar to the aforementioned detection method.

Measurement

Measurement can be performed by a conventionally known procedure according to a type of signal to be measured, by the naked eye or using a measurement apparatus. In addition, the intensity of the signal used in the correlation equation described below can be either a raw measured value or a score value of a group into which the measured value is categorized according to a range of the intensity of the signal. The score value are, for example, as follows:

Score 0: No signal detected;
Score 1: Weak signal detected;
Score 2: Signal clearly detected.

Correlation Equation

The correlation equation between the amount of the target substance and the intensity of the signal under the same condition as the abovementioned predetermined condition is constructed. The more data that is available on the amount of target substance and the intensity of the signal constituting the correlation equation, the greater the reliability of the correlation equation becomes. Thus, the data should be based on at least 2 samples containing different amounts of the target substance, and preferably based on at least 3 samples containing different amounts thereof.

The correlation equation between the amount of the target substance and the intensity of the signal is not limited to an equation indicating a direct correlation between the amount of the target substance and the intensity of the signal, and can be a correlation equation between parameters reflecting the amount of the target substance and the intensity of the signal.

Calculation

The amount of the target substance in a sample can be calculated by assigning a value of the intensity of the signal after development of the mixture to the resulting correlation equation.

Target Substance

The target substance which can be detected with the abovementioned detection method includes environmental pollutants, food and beverage contaminants, and substances used for clinical diagnosis such as, dioxin, endocrine disrupters, agrichemicals, PCB, organic mercury and the like, prion, mycotoxin, fugutoxin, antibiotics, funicides and the like, human immunoglobulin G, M, A and E, human albumin, human fibrinogen (fibrin and degradation product thereof), α-fetoprotein (AFP), C-reactive protein (CRP), myoglobin, carcinoembryonic antigen, hepatitis virus antigen, human chorionic gonadotropin (hCG), human placental lactogen (HPL), HIV antigen, allergen, bacterial toxin, bacterial antigen, enzyme, hormone (for example, human thyroid stimulating hormone (TSH) and insulin), and drugs that are contained in body fluid, urine, sputum, stool and the like.

Kit

The present invention includes a kit for detecting and/or quantifying a target substance. The kit includes: a first bound substance in which a first substance having an agglutinating substance containing a stimuli-responsive polymer binds to a first affinity substance having affinity to a target substance; a second bound substance in which a second substance, being hydrophilic, binds to a second affinity substance having affinity to the target substance; and a developing carrier for developing the bound substances. The first substance or the second substance preferably include colored particles. In addition, the first bound substance or the second bound substance preferably include a substance that produces color or luminescence on the developing carrier. Detailed descriptions for each component are already given above and therefore omitted.

EXAMPLES

Representative reagents used in Examples of the present invention are as follows:

PBS buffer: commercially available PBS at a 10× concentration (81 mM $Na_2HPO_4$, 14.7 mM $KH_2PO_4$, 26.8 mM KCl, 1370 mM NaCl, pH 7.4, manufactured by Nippon Gene Co., Ltd.) diluted to 1/10 (V/V) with purified water;

purified water: water purified by Direct-Q (trade name) manufactured by Millipore Corporation.

Example 1

In the present example, magnetic particles having surfaces thereof modified with anti-TSHβ antibody-bound temperature-responsive polymer, are used as the first bound substance, and anti-TSHα antibody-bound sodium polyacrylate is used as the second bound substance to detect human thyroid stimulating hormone (TSH).

Preparation of First Bound Substance

A biotinylated anti-human TSH antibody was prepared by Asahi Techno Glass Co., Ltd by biotinylating anti-human TSH antibody manufactured by Leinco Technologies, Inc. (Anti-Human Thyroid Stimulating Hormone Beta, clone: 195 mouse, class: Mouse IgG) using sulfo-NHS-Biotin.

250 µl of Therma-Max (Registered Trademark) LSA Streptavidin (0.4 mass %) manufactured by Magnabeat Inc. was taken in a microtube of 1.5 ml as the magnetic particles having surfaces thereof modified with streptavidin-bound temperature-responsive polymer, and then 50 µl of the biotinylated anti-human TSH antibody dissolved in the PBS buffer (0.75 mg/ml) was added thereto and inverted for 15 minutes at 4° C. The microtube was heated up to 37° C., the magnetic particles were collected using a magnet, and the supernatant was removed. 250 µl of PBS buffer was added thereto and cooled, thereby dispersing the magnetic particles. Furthermore, excessive amounts of biotin was added into the tube, to mask a biotin binding site of streptavidin. The microtube was heated up to 37° C. again, the magnetic particles were collected using a magnet, and the supernatant was removed, thereby preparing the magnetic particles having surfaces thereof modified with anti-human TSHβ antibody-bound temperature-responsive polymer.

In the tube containing the magnetic particles having surfaces thereof modified with anti-human TSH antibody-bound temperature-responsive polymer, 500 µl of PBS buffer (pH 7.4), including 0.5% (w/v) of BSA (manufactured by Sigma, Co.), 0.5% (w/v) of Tween (Registered Trademark) 20 and 10 mM EDTA, was added thereto and cooled to disperse. A dispersed solution of the first bound substance was thus obtained.

Preparation of Second Bound Substance

First, 6 mg of 2-mercaptoethanol was added to 1 ml of anti-human TSHα antibody (Anti-Human Thyroid Stimulating Hormone Alpha, clone: 176 mouse, Mouse IgG, manufactured by Leinco Technology, Inc., 1 mg/ml) as a second affinity substance having affinity to human thyroid stimulating hormone (TSH) as a target substance, and is reacted for 120 minutes at 37° C. After the reaction, 500 ml of PBS buffer was dialyzed using Slide-A-Lyzer (trade name) dialysis cassette and 10 KMWCO (manufactured by Pierce) to remove excessive 2-mercaptoethanol and condensed to 0.5 ml using an ultrafiltration membrane of 10000 in molecular-weight cutoff limit (Amicon Ultra-4 Ultracel 10k manufactured by Millipore Corporation), thereby obtaining a reduced antibody of mouse anti-human TSHα antibody. 0.5 ml of the reduced antibody and 100 µl of maleimide sodium polyacrylate were reacted overnight at 4° C., and then gel-filtrated using Superdex-20010/300 GL (manufactured by GE Healthcare), thereby preparing a labeled antibody. The labeled antibody (also referred to as a sodium polyacrylate-anti-human TSHα antibody-bound substance) was diluted with PBS buffer (pH 7.4) including 0.5% (w/v) of BSA (manufactured by Sigma, Co.), 0.5% (w/v) of Tween (Registered Trademark) 20 and 10 mM EDTA, such that protein concentration is 4 µg/ml, thereby preparing the second bound substance.

The abovementioned maleimide sodium polyacrylate was prepared as follows. First, in a three-neck flask of 100 ml provided with a nitrogen gas introduction tube, a thermometer, and an agitator, 2 g of acrylic acid (manufactured by Wako Pure Chemical Industries, Ltd.), 0.021 g of 2-aminoethanethiol (manufactured by Wako Pure Chemical Industries, Ltd.) and 0.023 g of azobisisobutyronitrile (manufactured by Wako Pure Chemical Industries, Ltd.) were dissolved in 50 ml of N,N-dimethylformamide, and nitrogen substitution was performed for one hour. Thereafter, polymerization reaction was performed at 70° C. for 7 hours. A reaction solution thus obtained was vacuum-concentrated to 10 ml, and reprecipitated by diethyl ether until a viscous substance became powdery. A white precipitate was separated by filtration and dried overnight in a vacuum dryer, thereby obtaining an amino group terminated polyacrylic acid (yield: 1.5 g). 0.5 g of the amino group terminated polyacrylic acid and 10 ml of N,N-dimethylformamide were put in a recovery flask of 50 ml provided with a nitrogen gas introduction tube and an agitator and dissolved. 3 mg of EMCS(N-(6-maleimidocaproiloxy)succinimido) (manufactured by Dojindo Laboratories) was added thereto and reacted overnight. A reaction solution thus obtained was vacuum-concentrated to 1 ml, and reprecipitated by diethyl ether until a viscous substance became powdery. A white precipitate was separated by filtration and dried overnight in a vacuum dryer, thereby obtaining a maleimide group terminated polyacrylic acid. A number average molecular weight of the maleimide group terminated polyacrylic acid was approximately 130000 (GPC system: manufactured by Shimadzu Corporation, column: manufactured by Tosoh Corporation, TSK gel Super AW3000, 6 mmID.× 150 mm, mobile phase: 0.1M sodium nitrate), and yield thereof was 0.4 g.

Preparation of Sample TSH; samples 2 and 3 were obtained by diluting a solution (concentration: 30 µg/ml) of human thyroid stimulating hormone manufactured by AspenBio Pharma, Inc. (activity: 8.5 IU/mg, WHO80/558) to 0.06 mIU/l and 0.0012 mIU/l, respectively, using VITROS (Registered Trademark) TSH Calibrator 1 (manufactured by Ortho Clinical Diagnostics). Sample 1 was prepared by performing the same procedure, except for human thyroid stimulating hormone not being included.

Development

150 µl of a dispersed solution of the first bound substance and 200 µl of a dispersed solution of the second bound substance were placed into microtubes and agitated for 1 second with a vortex mixer, 50 µl of each sample were placed thereinto and agitated with a vortex mixer, and then incubated for 5 minutes at room temperature (21° C.). A total amount of the reaction solution was removed from the tube and placed in a reaction tube kept at 37° C. in advance (see FIG. 3), and maintained at 37° C. for 5 minutes.

Thereafter, a membrane filter Hi-Flow Membrane #SNHF0400 (trade name) (manufactured by Millipore Corporation) of a size of 5 mm×50 mm, having a pore diameter of no greater than 0.1 µm, as the developing carrier, was immersed in the reaction solution in the reaction tube up to approximately 10 mm from a bottom end thereof, and left at rest for 1 minute. Subsequently, the membrane filter was gently pulled up and observed. The results are shown in FIG. 9.

Determination

Figure 9:
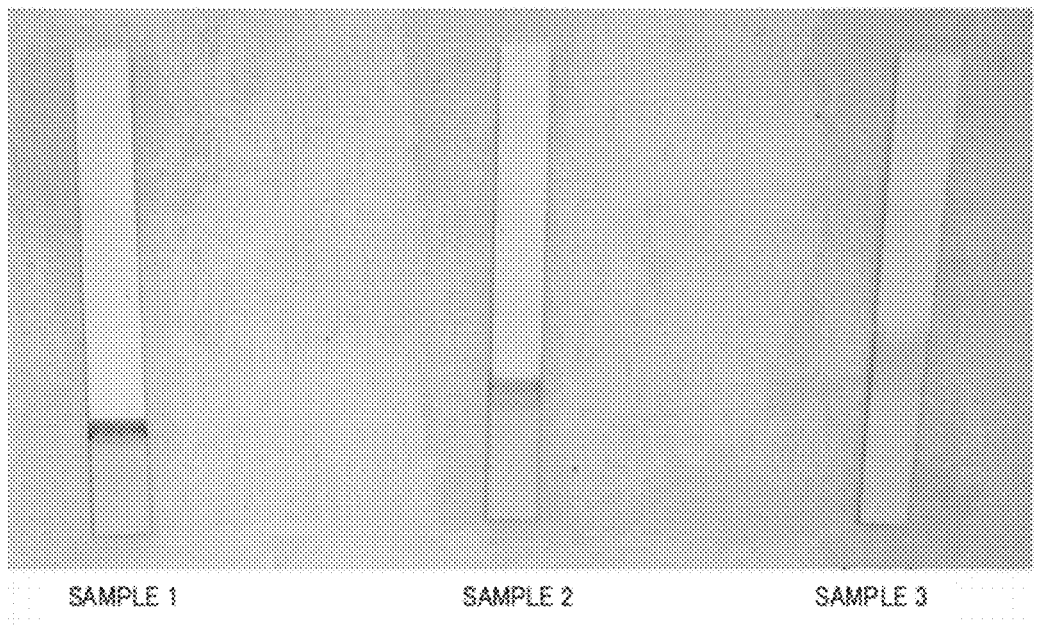
FIG. 9 is a photograph showing a result of conducting a method according to an Example of the present invention.

As shown in FIG. 9, with Sample 1 not containing the target substance, a brown band, resulting from the presence of a bound substance (magnetic particles) in an aggregate, was observed at a position corresponding to a meniscus (approximately 10 mm from the bottom end). On the contrary, with Samples 2 and 3 containing the target substance, a brown band was not observed at a position corresponding to a meniscus and a brown area was observed extensively. Therefore, this shows that in a case where a density of the brown band at a position corresponding to a meniscus is lighter than in the absence of the target substance, the target substance can be determined to be present in the sample. In addition, this shows that the target substance can be determined to be present in the sample also in a case where the brown area is not concentrated in the position of a meniscus and observed extensively.

Example 2

In the present example, magnetic particles having surfaces thereof modified with anti-HBs antibody-bound temperature-responsive polymer, are used as the first bound substance, and anti-HBs antibody-bound polyethyleneglycol is used as the second bound substance to detect HBs antibody.

Preparation of First Bound Substance

Anti-HBs monoclonal antibody manufactured by Institute of Immunology Co., Ltd. (antigen determinant: a, clone number: Hyb-824) was biotinylated using EZ-Link Sulfo-NHS-Biotin Kit, Product #21420 (trade name) (manufactured by Pierce Protein Research), according to a biotinylating method attached to the kit, thereby preparing biotinylated anti-HBs monoclonal antibody.

500 µl of Therma-Max (Registered Trademark) LSA Streptavidin (30) (0.2 mass %) manufactured by Magnabeat Inc., which is magnetic particles having surfaces thereof modified with temperature-responsive polymer, was taken in a microtube of 1.5 ml, and then 50 µl of the biotinylated anti-HBs monoclonal antibody dissolved in the PBS buffer (0.75 mg/ml) was added thereto and inverted for 15 minutes at 4° C. The microtube was heated up to 37° C., the magnetic particles were collected using a magnet, and the supernatant was removed, thereby preparing magnetic particles having surfaces thereof modified with anti-HBs monoclonal antibody-bound temperature-responsive polymer.

In the tube containing the magnetic particles having surfaces thereof modified with anti-HBs antibody-bound temperature-responsive polymer, 500 μl of PBS buffer (pH 7.4), including 0.5% (w/v) of BSA (manufactured by Sigma, Co.), 0.5% (w/v) of Tween (Registered Trademark) 20 and 10 mM EDTA, was added thereto and cooled to disperse the magnetic particles. A dispersed solution of the first bound substance was thus obtained.

Preparation of Second Bound Substance

Two kinds of reduced antibodies of anti-HBs monoclonal antibody were obtained in the same procedure as in Example 1, except for using anti-HBs monoclonal antibody manufactured by Institute of Immunology Co., Ltd. (antigen determinant: d, clone number: Hyb-3423) and anti-HBs monoclonal antibody manufactured by Institute of Immunology Co., Ltd. (antigen determinant: y, clone number: Hyb-3457) instead of anti-human TSHα antibody, and using 2-mercaptoethylamine hydrochloride instead of 2-mercaptoethanol. The second bound substance was prepared from these reduced antibodies, by obtaining two kinds of labeled antibodies in the same procedure as in Example 1, except for using maleimide polyethyleneglycol instead of maleimide sodium polyacrylate. The maleimide polyethyleneglycol used herein was SUNBRIGHT ME-400MA (trade name) manufactured by NOF CORPORATION, with weight-average molecular weight of 40000.

Preparation of Sample

Purified HBs antigen manufactured by Institute of Immunology Co., Ltd. was diluted to concentration of 1000 ng/ml with 0.5% BSA (manufactured by Sigma, Co.) and PBS buffer (pH 7.4). A positive sample (Sample 2) was obtained by diluting a dilution thus obtained with human serum determined to be negative using VITROS (Registered Trademark) HBs antigen (lot No. 2330) kit (manufactured by Ortho Clinical Diagnostics) to concentration of 10 ng/ml. In addition, the human serum was used as a negative sample (Sample 1).

Development

Development on the membrane filter was performed in the same procedure as in Example 1, except for using 100 μl of a dispersed solution of the first bound substance, 100 μl of a dispersed solution of the second bound substance, and 5 μl of the sample, and the membrane filter was observed. The results are shown in FIG. 10.

Determination

Figure 10:
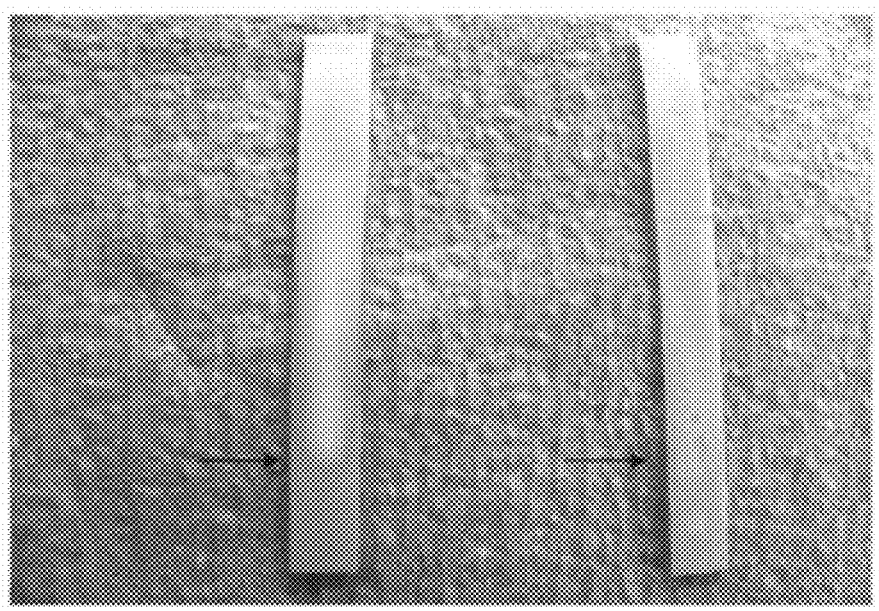
FIG. 10 is a photograph showing a result of conducting a method according to another Example of the present invention.

As shown in FIG. 10, with Sample 1 not containing the target substance, a brown band, resulting from the presence of a bound substance (magnetic particles) in an aggregate, was observed at a position corresponding to a meniscus (a position shown by an arrow in the diagram). On the contrary, with Sample 2 containing the target substance, a brown band was not observed at a position corresponding to a meniscus and a brown area was observed extensively. Therefore, this shows that in a case where a density of the brown band at a position corresponding to a meniscus is lighter than in the absence of the target substance, the target substance can be determined to be present in the sample. In addition, this shows that the target substance can be determined to be present in the sample also in a case where the brown area is not concentrated in the position of a meniscus and observed extensively.

EXPLANATION OF REFERENCE NUMERALS

10 First bound substance
11 Stimuli-responsive polymer
13 First antibody (first affinity substance)
15 Avidin
17 Biotin
19 Magnetic material
20 Second bound substance
21 Second substance
23 Second antibody (second affinity substance)
30 Developing carrier
40 Developing apparatus
41 Upper supporting member
42 Lower supporting member
43 Feed opening portion
44 Window portion
47 Filter
50 Target substance

The invention claimed is:

1. A method for detecting a target substance in a sample, comprising steps of:
    mixing a particle carrying a first bound substance in which a first substance containing a stimuli-responsive polymer binds to a first affinity substance having affinity to the target substance, a second bound substance in which a hydrophilic second substance binds to a second affinity substance having affinity to the target substance, and the sample, to obtain a mixture;
    placing the mixture under conditions to aggregate the stimuli responsive polymer and developing the mixture thus obtained on a developing carrier; or developing the mixture on a developing carrier and placing the mixture under conditions to aggregate the stimuli-responsive polymer;
    detecting a signal resulting from the presence of the first bound substance or the second bound substance on the developing carrier; and in a case where the signal is different from that detected in the absence of the target substance, determining that the target substance is present in the sample,
    wherein the first affinity substance and the second affinity substance can bind to different sites of the target substance, the hydrophilic second substance is capable of inhibiting aggregation of the stimuli-responsive polymer,
    wherein the developing carrier is a chromatography carrier that is a perforated membrane, such that a non-aggregated body having a diameter smaller than a pore diameter of the developing carrier moves on the developing carrier and an aggregate having a diameter larger than the pore diameter of the developing carrier does not move on the developing carrier, and
    wherein the conditions to aggregate the stimuli-responsive polymer comprise a stimulus, such that the stimuli-responsive polymer aggregates in response to the stimulus.

2. The method according to claim 1, wherein the target substance is determined to be present in the sample in a case where intensity of the signal resulting from the presence of the first bound substance is lower than that in the absence of the target substance.

3. The method according to claim 1, wherein the mixture is developed on the developing carrier after removing an aggregated substance of the first bound substance,
    and the target substance is determined to be present in the sample in a case where intensity of the signal resulting from the presence of the first bound substance is higher than that in the absence of the target substance.

4. A method for quantifying a target substance in a sample, comprising steps of:
    mixing a particle carrying a first bound substance in which a first substance containing a stimuli-responsive polymer binds to a first affinity substance having affinity to the target substance, a second bound substance in which a hydrophilic second substance binds to a second affinity substance having affinity to the target substance, and the sample, to obtain a mixture;

placing the mixture under conditions to aggregate the stimuli-responsive polymer and developing the mixture on a developing carrier; or developing the mixture on a developing carrier and placing the mixture under conditions to aggregate the stimuli-responsive polymer;

determining intensity of a signal resulting from the presence of the first bound substance or the second bound substance on the developing carrier; and calculating an amount of the target substance in the sample based on a correlation equation between an amount of the target substance and intensity of the signal under the predetermined conditions, wherein the first affinity substance and the second affinity substance can bind to different sites of the target substance, the hydrophilic second substance is capable of inhibiting aggregation of the stimuli-responsive polymer, wherein the developing carrier is a chromatography carrier that is a perforated membrane, such that a non-aggregated body having a diameter smaller than a pore diameter of the developing carrier moves on the developing carrier and an aggregate having a diameter larger than the pore diameter of the developing carrier does not move on the developing carrier, and wherein the conditions to aggregate the stimuli-responsive polymer comprise a stimulus, such that the stimuli-responsive polymer aggregates in response to the stimulus.

5. The method according to claim 4, wherein a signal resulting from the presence of an aggregate of the first bound substance is determined.

6. The method according to claim 4, wherein the mixture is developed on the developing carrier after removing an aggregated substance of the first bound substance, and intensity of a signal resulting from the presence of the first bound substance is determined.

7. The method according to claim 1, wherein the first bound substance includes colored particles and the signal depends on a color resulting from the presence of the colored particles.

8. The method according to claim 1, wherein the first bound substance or the second bound substance includes a substance that produces color or luminescence on the developing carrier, the signal depends on a color or light resulting from the presence of the substance that produces color or luminescence.

9. A kit for at least any one of detection and quantification of a target substance, comprising:

a particle carrying a first bound substance in which a first substance containing a stimuli-responsive polymer binds to a first affinity substance having affinity to the target substance wherein the stimuli-responsive polymer is capable of aggregating in response to a stimulus;

a second bound substance in which a second substance, being hydrophilic, binds to a second affinity substance having affinity to the target substance, wherein the hydrophilic second substance is capable of inhibiting aggregation of the stimuli-responsive polymer; and wherein the first affinity substance and the second affinity substance are capable of binding to different sites of the target substance; and a developing carrier for developing the bound substances, wherein the developing carrier is a chromatography carrier that is a perforated membrane, such that, in use, a non-aggregated body having a diameter smaller than a pore diameter of the developing carrier moves on the developing carrier and an aggregate having a diameter larger than the pore diameter of the developing carrier does not move on the developing carrier.

10. The kit according to claim 9, wherein the first bound substance includes colored particles.

11. The kit according to claim 9, wherein the first bound substance or the second bound substance includes a substance that produces color or luminescence on the developing carrier.

12. The method according to claim 4, wherein the first bound substance includes colored particles and the signal depends on a color resulting from the presence of the colored particles.

13. The method according to claim 4, wherein the first bound substance or the second bound substance includes a substance that produces color or luminescence on the developing carrier, the signal depends on a color or light resulting from the presence of the substance that produces color or luminescence.

14. The kit according to claim 12, wherein the first bound substance or the second bound substance includes a substance that produces color or luminescence on the developing carrier.

* * * * *